United States Patent [19]
Panetta et al.

[11] Patent Number: 5,981,523
[45] Date of Patent: Nov. 9, 1999

[54] COMPOUNDS AND METHODS FOR TREATING MULTIPLE SCLEROSIS

[75] Inventors: Jill A Panetta, Zionsville; Michael L Phillips, Indianapolis, both of Ind.

[73] Assignee: Eli Lilly and Company, Indianapolis, Ind.

[21] Appl. No.: 08/894,201

[22] PCT Filed: Dec. 16, 1996

[86] PCT No.: PCT/US96/20047

§ 371 Date: Aug. 14, 1997

§ 102(e) Date: Aug. 14, 1997

[87] PCT Pub. No.: WO97/21692

PCT Pub. Date: Jun. 19, 1997

[30] Foreign Application Priority Data

Feb. 5, 1996 [GB] United Kingdom ............ 9602269

[51] Int. Cl.[6] ............................................ A61K 31/54
[52] U.S. Cl. ............ 514/227.5; 544/58.2; 544/58.4; 544/6
[58] Field of Search .................. 544/58.2, 58.4, 544/6; 514/227.5

[56] References Cited

U.S. PATENT DOCUMENTS

| | | | |
|---|---|---|---|
| 5,229,382 | 7/1993 | Chakrabarti et al. | 514/220 |
| 5,457,101 | 10/1995 | Greenwood et al. | 514/220 |
| 5,556,841 | 9/1996 | Kawashima et al. | 514/61 |

FOREIGN PATENT DOCUMENTS

| | | |
|---|---|---|
| 0 434 394 | 6/1991 | European Pat. Off. |
| 0 666 261 | 8/1995 | European Pat. Off. |
| WO 90/01929 | 3/1990 | WIPO |

OTHER PUBLICATIONS

Lehr, et al., "Sustituted 3–Thiomorpholinones", vol. 6, pp. 136–141, 1963.
Sohda, et al., *Chem. Pharm. Bull.*, vol. 30, No. 10, pp. 3563–3573, 1982.
Chem. Abstract, Imai, et al., vol. 106, No. 25, 1987.

*Primary Examiner*—John M. Ford

*Attorney, Agent, or Firm*—Nelsen L. Lentz; Arleen Palmberg

[57] ABSTRACT

This invention provides thiomorpholinone compounds useful for treating multiple sclerosis of formula I

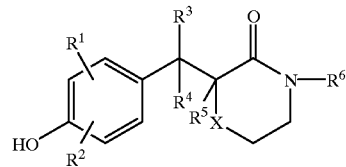

(I)

wherein:
R[1] and R[2] are each independently selected from $C_1$–$C_8$ alkyl; $C_2$–$C_8$ alkenyl; $C_2$–$C_8$ alkynyl; $C_1$–$C_8$ alkyloxy; $C_1$–$C_8$ alkylthio; trifluoromethyl; $C_1$–$C_4$ alkyl substituted with phenyl; phenyl; F; Cl; $NO_2$; phenoxy; $C_1$–$C_4$ alkyl substituted with phenoxy; thiophenyl; $C_1$–$C_4$ alkylthiophenyl; —COOR[7]; —N(R[7])$_2$ or —N(R[7])$SO_2$R[7] where each R[7] is independently hydrogen or $C_1$–$C_6$ alkyl;

R[3] is H or $C_1$–$C_4$ alkyl;

R[4] and R[5] are each individually H, or when taken together form a bond;

R[6] is H; $C_1$–$C_8$ alkyl; $C_2$–$C_8$ alkenyl; $C_2$–$C_8$ alkynyl; —$SO_2CH_3$; —$(CH_2)_n NR^8 R^9$; —$(CH_2)_n CO_2 R^8$; —$(CH_2)_n OR^8$ where n is an integer from 1 to 6, both inclusive, and R[8] and R[9] are each independently hydrogen; $C_1$–$C_6$ alkyl; $C_2$–$C_6$ alkenyl; $C_2$–$C_6$ alkynyl; phenyl; $C_1$–$C_4$ alkyl substituted with phenyl; —$(CH_2)_q$OH; or $(CH_2)_q S(C_1$–$C_4$alkyl) where q is an integer from 2 to 6, both inclusive; and

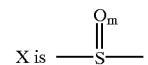

where m is 0 or 1;

or a pharmaceutically acceptable salt or optical isomer thereof.

4 Claims, No Drawings

COMPOUNDS AND METHODS FOR TREATING MULTIPLE SCLEROSIS

This is a 35 U.S.C. § of PCT/US96/20047, filed Dec. 16, 1996.

This invention relates to novel thiomorpholinone compounds useful for treating multiple sclerosis.

Multiple Sclerosis was first described as a clinical entity in 1868. Clinically, it is a highly variable disease, which usually begins between the second and fifth decades of life. The most common signs of multiple sclerosis are sensory and visual motor dysfunction. In the chronic form the patient has periods of remission, but with each remission there is greater neurological dysfunction.

Macroscopically, multiple sclerosis involves lesions of 1 to 4 cm called plaques scattered throughout the white matter of the central nervous system. Microscopically, the disease is characterized by a break down of the nervous systems myelin sheath. There is also a loss of myelin basic protein in the area of the lesions.

The etiology and pathogenesis of multiple sclerosis remains obscure. Both chronic infectious agents and autoimmunity have been involved and, in fact, both might be important.

Meanwhile, the need continues for safer, better calibrated drugs which will either slow the process of neurodegeneration associated with multiple sclerosis or even prevent such neurodegeneration altogether. The present invention provides new thiomorpholinone compounds useful for treating multiple sclerosis. These compounds provide for safe and efficacious treatment of multiple sclerosis by slowing the process of neurodegeneration associated with such disease.

This invention provides compounds of the formula (I)

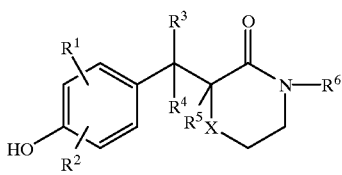

(I)

wherein:

$R^1$ and $R^2$ are each independently selected from $C_1$–$C_8$ alkyl; $C_2$–$C_8$ alkenyl; $C_2$–$C_8$ alkynyl; $C_1$–$C_8$ alkyloxy; $C_1$–$C_8$ alkylthio; trifluoromethyl; $C_1$–$C_4$ alkyl substituted with phenyl; phenyl; F; Cl; $NO_2$; phenoxy; $C_1$–$C_4$ alkyl substituted with phenoxy; thiophenyl; $C_1$–$C_4$ alkylthiophenyl; —$COOR^7$; —$N(R^7)_2$ or —$N(R^7)SO_2R^7$ where each $R^7$ is independently hydrogen or $C_1$–$C_6$ alkyl;

$R^3$ is H or $C_1$–$C_4$ alkyl;

$R^4$ and $R^5$ are each individually H, or when taken together form a bond;

$R^6$ is H; $C_1$–$C_8$ alkyl; $C_2$–$C_8$ alkenyl; $C_2$–$C_8$ alkynyl; —$SO_2CH_3$; —$(CH_2)_nNR^8R^9$; —$(CH_2)_nCO_2R^8$; —$(CH_2)_nOR^8$ where n is an integer from 1 to 6, both inclusive, and $R^8$ and $R^9$ are each independently hydrogen; $C_1$–$C_6$ alkyl; $C_2$–$C_6$ alkenyl; $C_2$–$C_6$ alkynyl; phenyl; $C_1$–$C_4$ alkyl substituted with phenyl; —$(CH_2)_qOH$; or $(CH_2)_qS(C_1$–$C_4$alkyl) where q is an integer from 2 to 6, both inclusive; and

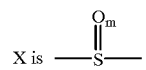

X is —S— where m is 0 or 1;

or a pharmaceutically acceptable salt or optical isomer thereof.

According to a further aspect of the present invention there are provided pharmaceutical compositions comprising as active ingredient a compound of Formula I or a pharmaceutically acceptable salt thereof, in association with one or more pharmaceutically acceptable diluents, carriers and excipients thereof.

The present invention also provides a method for treating multiple sclerosis in a mammal in need of such treatment, which comprises administering to said mammal a therapeutically effective amount of a compound, or pharmaceutically acceptable salt or isomer thereof, of the formula I.

Other objects, features and advantages of the present invention will become apparent from the subsequent description and the appended claims.

As used herein, the term "$C_1$–$C_8$ alkyl" represents a straight or branched alkyl chain having from one to eight carbon atoms. Typical $C_1$–$C_8$ alkyl groups include methyl, ethyl, n-propyl, isopropyl, n-butyl, sec-butyl, isobutyl, t-butyl, n-pentyl, isopentyl, neopentyl, heptyl, hexyl, octyl and the like. The term "$C_1$–$C_8$ alkyl" includes within its definition the terms "$C_1$–$C_4$ alkyl" and "$C_1$–$C_6$ alkyl".

"$C_1$–$C_4$ alkyl substituted with phenyl" represents a straight or branched chain alkyl group having from one to four carbon atoms attached to a phenyl ring. Typical $C_1$–$C_4$ alkylphenyl groups include benzyl, phenylethyl, phenylpropyl, 1-methyl-1-phenylethyl, phenylbutyl, 2-methyl-3-phenylpropyl, and 1,1-dimethyl-2-phenylethyl.

The term "$C_1$–$C_4$ alkylthiophenyl" represents a straight or branched chain alkyl group having from one to four carbon atoms attached to a thiophenyl moiety. Typical $C_1$–$C_4$ alkylthiophenyl groups include methylthiophenyl, 2-methylethylthiophenyl, ethylthiophenyl, isobutylthiophenyl and the like.

In a similar fashion, the term "$C_1$–$C_4$ alkyl substituted with phenoxyl" represents a straight or branched chain alkyl group having from one to four carbon atoms substituted with a phenoxy moiety. Typical $C_1$–$C_4$ alkyloxyphenyl groups include phenoxymethyl, phenoxyethyl, phenoxypropyl and the like.

"$C_1$–$C_8$ alkyloxy" represents a straight or branched alkyl chain having one to eight carbon atoms, which chain is attached to the remainder of the molecule by an oxygen atom. Typical $C_1$–$C_8$ alkyloxy groups include methoxy, ethoxy, propoxy, isopropoxy, butoxy, isobutoxy, sec-butoxy, tert-butoxy, pentoxy, hexoxy, heptoxy, and the like. The term "$C_1$–$C_8$ alkoxy" includes within its definition the term "$C_1$–$C_4$ alkoxy".

"$C_1$–$C_8$ alkylthio" represents a straight or branched alkyl chain having one to eight carbon atoms, which chain is attached to the remainder of the molecule by a sulfur atom. Typical $C_1$–$C_8$ alkylthio groups include methylthio, ethylthio, propylthio, butylthio, tert-butylthio, octylthio and the like. The term "$C_1$–$C_8$ alkylthio" includes within its definition the term "$C_1$–$C_4$ alkylthio".

The term "$C_2$–$C_6$ alkenyl" refers to straight and branched chain radicals of two to six carbon atoms, both inclusive, having one or more double bonds. As such, the term includes ethylene, propylene, 1-butene, 2-butene, 2-methyl-1-propene, 1-pentene, 2-methyl-2-butene and the like.

The term "$C_2$–$C_6$ alkynyl" refers to straight and branched chain radicals of two to six carbon atoms, both inclusive, having one or more triple bonds. As such, the term includes acetylene, propyne, 1-butyne, 2-hexyne, 1-pentyne, 3-ethyl-1-butyne and the like.

The term "pharmaceutically acceptable salts" refers to salts of the compounds of the above formulae which are substantially non-toxic to living organisms. Typical pharmaceutically acceptable salts include those salts prepared by reaction of the compounds of the above formulae with a pharmaceutically acceptable mineral or organic acid, or a pharmaceutically acceptable alkali metal or organic base, depending on the types of substituents present on the compounds of the formulae.

Examples of pharmaceutically acceptable mineral acids which may be used to prepare pharmaceutically acceptable salts include hydrochloric acid, phosphoric acid, sulfuric acid, hydrobromic acid, hydroiodic acid, phosphorous acid and the like. Examples of pharmaceutically acceptable organic acids which may be used to prepare pharmaceutically acceptable salts include aliphatic mono and dicarboxylic acids, oxalic acid, carbonic acid, citric acid, succinic acid, phenyl-substituted alkanoic acids, aliphatic and aromatic sulfonic acids and the like. Such pharmaceutically acceptable salts prepared from mineral or organic acids thus include hydrochloride, hydrobromide, nitrate, sulfate, pyrosulfate, bisulfate, sulfite, bisultite, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like.

Many compounds of formulae I which contain a carboxy group may be converted to a pharmaceutically acceptable salt by reaction with a pharmaceutically acceptable alkali metal or alkaline-earth metal or organic or inorganic base. Examples of pharmaceutically acceptable alkali or alkaline-earth metal bases include compounds of the general formula $MOR^{13}$, where M represents an alkali or alkaline earth metal atom, e.g. sodium, potassium, lithium, calcium or barium and $R^{13}$ represents hydrogen or $C_1–C_4$ alkyl. Examples of pharmaceutically acceptable organic and inorganic bases which may be used to prepare pharmaceutically acceptable salts include sodium carbonate, sodium bicarbonate, ammonia, amines such as triethanolamine, triethylamine, ethylamine, and the like.

It should be recognized that the particular anion or cation forming a part of any salt of this invention is not critical, so long as the salt, as a whole, is pharmacologically acceptable and as long as the anion or cationic moiety does not contribute undesired qualities.

Depending upon the definitions of $R^1$, $R^2$ and $R^3$, the compounds of Formula I may exist in various isomeric forms. This invention is not related to any particular isomer but includes all possible individual isomers and racemates.

Preferred Compounds of the Invention

A preferred genus of compounds includes those compounds wherein $R^1$, $R^2$, $R^3$, $R^4$, $R^5$ and m are as set forth for formula I, and $R^6$ is hydrogen, $C_1–C_6$ alkyl, $C_2–C_6$ alkenyl or —$(CH_2)_nOR^8$ where n is 2 and $R^8$ is hydrogen.

Of this preferred genus, those compounds in which

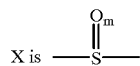

where m is 0 are more preferred.

Of this more preferred genus, those compounds in which $R^6$ is hydrogen are especially preferred.

Of this especially preferred genus, those compounds in which $R^1$ and $R^2$ are each independently $C_1–C_8$ alkyl; $C_1–C_8$ alkyloxy; $C_1–C_4$ alkyl substituted with phenyl; phenyl; F; Cl; $NO_2$; phenoxy; $C_1–C_4$ alkylthiophenyl; —$COOR^7$ or —$N(R^7)SO_2R^7$, where each $R^7$ is independently hydrogen or $C_1–C_6$ alkyl, are particularly preferred.

Of this particularly preferred genus, those compounds in which $R^1$ and $R^2$ are each independently $C_1–C_8$ alkyl (especially $C_1–C_4$ alkyl), or $C_1–C_8$ alkoxy (especially $C_1–C_6$ alkoxy), are more particularly preferred.

The skilled artisan will readily recognize that compounds encompassed by the instant invention include 2-[[3,5-bis(1,1-dimethylethyl)-4-hydroxyphenyl]methylene]-4-(2-hydroxyethyl)-3-thiomorpholinone;

2-[[3,5-bis(1,1-dimethylethyl)-4-hydroxyphenyl]methylene]-4-[2-(dimethylamino)ethyl]-3-thiomorpholinone;

2-[[3,5-bis(1,1-dimethylethyl)-3-hydroxyphenyl]methylene]-4-(methylsulfonyl)-3-thiomorpholinone;

2-[(4-hydroxy-3,5-di-2-propenylphenyl)methylene]-4-methyl-3-thiomorpholinone;

2-[(4-hydroxy-3,5-dinitrophenyl)methylene]-4-methyl-3-thiomorpholinone;

2-[(3,5-dichloro-4-hydroxyphenyl)methylene]-4-methyl-3-thiomorpholinone;

2-[[3-ethoxy-4-hydroxy-5-[(phenylthio)methyl]phenyl]methylene]-4-methyl-3-thiomorpholinone;

2-[[3,5-bis(1,1-dimethylethyl)-4-hydroxyphenyl]methylene]-4-(2-propenyl)-3-thiomorpholinone;

2-[[3,5-bis(1,1-dimethylethyl-4-hydroxyphenyl]methylene]-3-thiomorpholinone

2-[[[4-hydroxy-5(1-pentenyl)-3-phenyl]phenyl]methylene]-4-methyl-3-thiomorpholinone;

±2-[[3-(2-pentynyl)-4-hydroxy-5-phenoxyphenyl]methyl]-4-methyl-3-thiomorpholinone;

±2-[[2-trifluoromethyl-4-hydroxy-3-(2,3-dimethylpentyl)phenyl]methyl]-4-methyl-3-thiomorpholinone;

2-[[(3-fluoro-4-hydroxy-6-methylthio)phenyl]methylene]-4-methyl-3-thiomorpholinone;

±2-[[(4-hydroxy-2-methyl-6-thiophenyl)phenyl]methyl]-4-methyl-3-thiomorpholinone;

2-[(3,5-diethylamino-4-hydroxyphenyl)methylene]-4-methyl-3-thiomorpholinone;

2-[[[3-(2-pentynyl)-4-hydroxy-5-phenoxypropyl]phenyl]methyl]-4-methyl-3-thiomorpholinone;

2-[[[4-hydroxy-2,6-bis(sulfonamido)]phenyl]methylene]-4-methyl-3-thiomorpholinone;

±2-[[(3-carboxy-4-hydroxy-5-dimethylethyl)phenyl]methyl]-4-methyl-3-thiomorpholinone;

2-[(4-hydroxy-2-methoxycarbonyl-6-ethylphenyl)methylene]-4-methyl-3-thiomorpholinone;

±2-[[[4-hydroxy-3-methyl-5[N-propyl-N-methylsulfonylamino]phenyl]methyl]-4-methyl-3-thiomorpholinone;

2-[[3,5-bis(1,1-dimethylethyl)-4-hydroxyphenyl]methylene]-4-isopentyl-3-thiomorpholinone;

2-[[3,5-bis(1,1-dimethylethyl)-4-hydroxyphenyl]methyl]-4-(2-hexynyl)-3-thiomorpholinone;

2-[[3,5-bis(1,1-dimethylethyl)-4-hydroxyphenyl]methylene]-4-ethynyl-3-thiomorpholinone;

2-[[3,5-bis(1,1-dimethylethyl)-4-hydroxyphenyl]methyl]-4-[4-(diphenylamino)butyl]-3-thiomorpholinone hydrochloride salt;

2-[[3,5-bis(1,1-dimethylethyl)-4-hydroxyphenyl]methylene]-4-[2-(N,N-bis(2-propenyl)aminoethyl-3-thiomorpholinone;

2-[[3,5-bis(1,1-dimethylethyl)-4-hydroxyphenyl]methyl]-4-[3-(diethynylamino)propyl]-3-thiomorpholinone oxaylic acid salt;

2-[[3,5-bis(1,1-dimethylethyl)-4-hydroxyphenyl]methyl]-4-[[3-(2-hydroxyethyl)amino]propyl]-3-thiomorpholinone;

2-[[3,5-bis(1,1-dimethylethyl)-4-hydroxyphenyl]methyl]-4-[[[3-(N,N-dimethylamino)ethyl]amino]propyl]-3-thiomorpholinone citric acid salt;

2-[[3,5-bis(1,1-dimethylethyl)-4-hydroxyphenyl]
methylene]-4-[[3-ethylphenylamino]propyl]-3-
thiomorpholinone hydrochloride salt;

±2-[[3,5-bis(1,1-dimethylethyl)-4-hydroxyphenyl]methyl]-
4-[2-(carboxyethyl)ethyl]-3-thiomorpholinone;

±2-[[3,5-bis(1,1-dimethylethyl)-4-hydroxyphenyl]methyl]-
4-[2-(ethoxycarbonyl)ethyl]-3-thiomorpholinone sodium
salt;

2-[[3,5-bis(1,1-dimethylethyl)-4-hydroxyphenyl]
methylene]-4-[3-[2-(methylthio)ethyl]amino]propyl-3-
thiomorpholinone;

2-[[3,5-bis(1,1-dimethylethyl)-4-hydroxyphenyl]
methylene]-4-(3-ethoxypropyl)-3-thiomorpholinone;

2-[[3,5-bis(1,1-dimethylethyl)-4-hydroxyphenyl]-
ethylmethylene]-4-methyl-3-thiomorpholinone.

2-[[3,5-bis(1,1-dimethylethyl)-4-hydroxyphenyl]-
ethylmethyl]-4-methyl-3-thiomorpholinone.

Synthesis Methods

Scheme I

The compounds of formula I, where $R^4$ is hydrogen, are prepared according to the reaction scheme I outlined below.

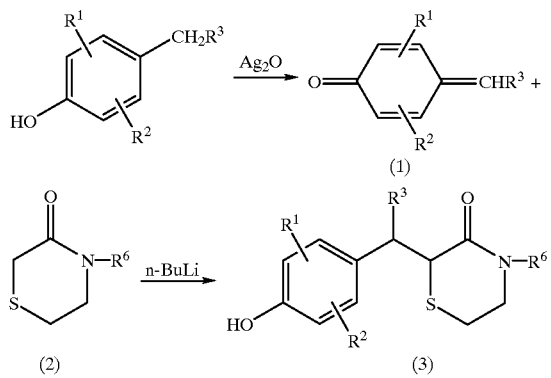

In the above reaction scheme, an appropriately substituted phenol, dissolved in an aprotic polar solvent such as tetrahydrofuran (THF), is reacted with a molar excess of a metal oxide, such as silver oxide, to prepare the substituted quinone methide (1). The reaction is conducted at temperatures of from about 0° C. to reflux, preferably at about 25° C.

A 4-substituted 3-thiomorpholinone starting material (2) can be readily prepared by reacting 3-thiomorpholinone with an appropriately substituted halide such as methyl or ethyl iodide, or methylsulfonyl chloride.

The substituted thiomorpholinone starting material (2) is then treated with a molar excess of an organolithium base, such as n-butyl lithium, to produce the lithium enolate. The reaction is conducted in an aprotic polar solvent, such as THF, at a temperature of from about 0° C. to about 25° C. preferably about 25° C.

The resultant lithium enolate solution is then reacted with the quinone methide (1) at a temperature of from about 0° C. to reflux, preferably about 25° C. to produce (3). The desired product (3) can be chromatographically purified using silica gel as the stationary phase and ethyl acetate in hexane as the mobile phase.

Depending on the substituents at $R^3$, $R^4$ and $R^5$, the compounds of the present invention may have one, two or three stereocenters. The method and compounds of the present invention encompass the diastereomers and the racemates and their individual stereoisomers. Diasteromeric pairs may be readily separated by standard techniques such as chromatography or crystallization. The stereoisomers may be obtained according to procedures well known in that art. For example, the racemate can be resolved by treating the mixture with diisopropyl tartrate and t-butyl hydroperoxide, as described in U.S. Pat. No. 5,216,002, herein incorporated by reference.

Scheme II

The compounds of formula I, where $R^4$ and $R^5$ taken together form a bond, are prepared according to the following general procedure.

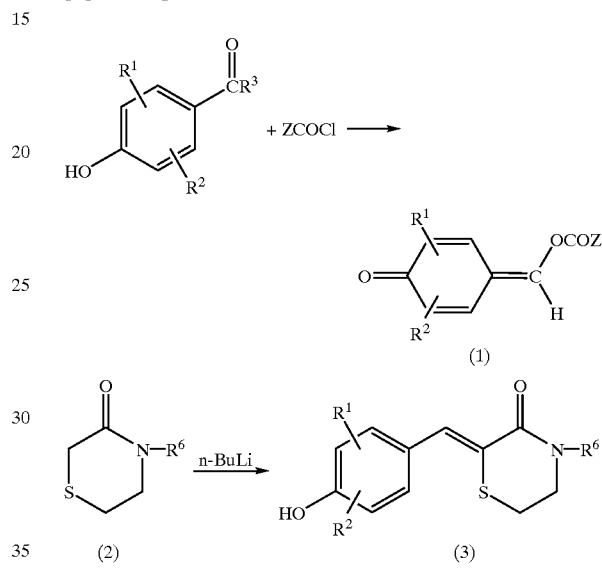

In the above Scheme II, an appropriately substituted p-hydroxybenzaldehyde or alkyl-p-hydroxyphenyl ketone is dissolved in a halogenated hydrocarbon such as dichloromethane and then reacted at room temperature with triethylamine and an acylating agent of the formula ZCOCl where Z is the residue of a protecting group, such as pivaloyl chloride or acetyl chloride, to prepare a protected benzaldehyde or phenyl ketone starting material (1).

The lithium enolate of a 4-substituted-3-thiomorpholinone, prepared as described in Scheme I above, is then dissolved in an aprotic solvent such as THF and the solution is cooled to from about −78° C. to about −20° C., preferably about −78° C. The enolate solution is reacted with a molar excess of the protected benzaldehyde (1) to produce the thiomorpholinone (3).

Oxidation of the thiomorpholinones prepared by the above schemes to produce the sulfoxide can be readily accomplished by treating the thiomorpholinone with an oxidant such as metachloroperbenzoic acid (m-CPBA) at temperatures of from about −20° C. to about 25° C. The reaction is preferably carried out in a halogenated hydrocarbon solvent such as methylene chloride. One mole of m-CPBA, per mole of (3), is required to produce the sulfoxide, and the reaction is substantially complete within an hour.

The sulfoxide can be purified using standard recrystallization procedures in a suitable organic solvent such as ethyl acetate/hexane. Further recrystalization may be accomplished with dichloromethane/hexane to give the desired product as the dichloromethane solvate.

Preparation of the 4-alkyl-3-thiomorpholinone starting material (2) can be achieved by an N-alkylation reaction using a suitable $R^6$ containing halide, such as iodide or bromide, to provide the corresponding N-substituted derivatives; i.e., those compounds of formula I where $R^6$ is $C_1-C_8$ alkyl, $C_2-C_8$ alkenyl, $C_2-C_8$ alkynyl, $—SO_2CH_3$, $—(CH_2)_n NR^8R^9$, $—(CH_2)_nCO_2R^8$ where n is an integer from 1 to 6, both inclusive and $R^8$ and $R^9$ are each independently hydrogen, $C_1-C_6$ alkyl, $C_2-C_6$ alkenyl, $C_2-C_6$ alkynyl, phenyl, $C_1-C_4$ alkylphenyl, $—(CH_2)_qOH$, $—(CH_2)_qN(C_1-C_4alkyl)_2$ or $(CH_2)_qS(C_1-C_4alkyl)$ where q is an integer from 2 to 6, both inclusive. For example, 4-methyl-3-thiomorpholinone can be prepared by treating a solution of 3-thiomorpholinone in THF with a 60% NaH dispersion followed by methyl iodide.

It will be readily appreciated by one skilled in the art that the substituted benzaldehyde, hydroxyphenylketone and substituted phenol starting materials are either commercially available or can be readily prepared by known techniques from commercially available starting materials. For example, p-hydroxybenzaldehyde may be alkylated under Friedel-Crafts conditions to yield an alkylated benzaldehyde which may in turn itself be alkylated.

Compounds where $R^1$ and $R^2$ in the starting material area each independently selected from $COOR^7$, $—N(R^7)_2$ or $—N(R^7)SO_2R^7$, where $R^7$ is hydrogen, will require the use of a protecting group, as described in the standard text "Protecting Groups in Organic Synthesis," 2nd Edition (1991), by Greene and Werts. The protecting group may be readily removed by conventional techniques after the final (linkage) step. Amine protecting groups may include acetyl while t-butyl may be used to protect acid functionalities.

All other reactants used to prepare the compounds in the instant invention are commercially available.

The following examples further illustrate the preparation of the compounds of this invention. The examples are illustrative only and are not intended to limit the scope of the invention in any way.

EXAMPLE 1

Preparation of 2-[[3,5-Bis(1,1-dimethylethyl)-4-hydroxyphenyl]methyl]-4-methyl-3-thiomorpholinone.

A. 4-methyl-3-thiomorpholinone

To a stirred solution of 3-thiomorpholinone (3.38 g, 28.8 mmol) in tetrahydrofuran (288 ml) was added 60% sodium hydride dispersion (1.27 g, 31.7 mmol) followed by methyl iodide (1.80 ml, 28.8 mmol). After stirring for 2 hours, the reaction was quenched with water and concentrated in vacuo. The resulting aqueous suspension was diluted with dichloromethane and acidified with 1N hydrochloric acid. Drying over sodium sulfate and evaporation of the dichloromethane layer gave a solid which was chromatographed on silica gel. Elution with 6 L of a 10–50% acetone in hexane gradient yielded 4-methyl-3-thiomorpholinone (3.02 g, 80%):

$^1$H NMR (CDCl$_3$) ∂ 3.65 (t, J=6 Hz, 2H), 3.35 (s, 2H), 3.05 (s, 3H), 2.9 (t, J=6 Hz, 2H).

B. 2-[[3,5-Bis(1,1-dimethylethyl)-4-hydroxyphenyl] methyl]-4-methyl-3-thiomorpholinone 4-methyl-3-thiomorpholinone (1.88 g, 14.3 mmol) dissolved in tetrahydrofuran (72 ml) was cooled to 0° C. and treated with 1.37M n-butyl lithium in hexane (20.9 ml, 28.7 mmol). After five minutes, the cold bath was removed. Ten minutes later a solution of 2,6-di-t-butyl-quinone methide, prepared by adding silver oxide (33.2 g, 143 mmol) to 2,6-di-t-butyl-4-methyl-phenol (BHT) (3.16 g, 14.3 mmol) in tetrahydrofuran (72 ml) stirring for 30 minutes and filtering, was added dropwise over 20 min. The reaction was stirred for three hours, quenched with 1N hydrochloric acid, and evaporated to an aqueous suspension. The crude product was extracted into ethyl acetate, dried over sodium sulfate and concentrated in vacuo. Chromatography on silica gel eluting with 8 L of a 0–50% ethyl acetate in hexane gradient yielded desired product (2.0 g, 40%):

$^1$H NMR (CDCl$_3$) ∂ 7.1 (s, 2H), 5.15 (s, 1H), 3.7–3.4 (m, 4H), 3.1 (s, 3H), 2.85 (dd, J=15, 9 Hz, 1H), 2.75 (t, J=6 Hz, 2H), 1.45 (S, 18H);

FD MS 349 (M$^+$);

Elemental Analysis for $C_{20}H_{31}NO_2S$: Theory: C, 68.72; H, 8.94; N, 4.01. Found: C, 68.95; H, 8.92; N, 4.23.

EXAMPLE 2

Preparation of (−)2-[[3,5-bis(1,1-dimethylethyl)-4-hydroxyphenyl]methyl]-4-methyl-3-thiomorpholinone.

To a stirred suspension of 4 Å molecular sieves (1.05 g) in methylene chloride (25 ml) was added titanium tetraisopropoxide (0.45 ml, 1.5 mmol), (+)diisopropyl tartrate (0.63 ml, 3.0 mmol), and deionized water (27 ml, 1.5 mmol), respectively. The suspension was allowed to stir at room temperature for 20 minutes before addition of 2-[[3,5-bis(1,1-dimethylethyl)-4-hydroxyphenyl]methyl]-4-methyl-3-thiomorpholinone (0.87 g, 2.5 mmol). After dissolution of the sulfide, the reaction was cooled to −20° C. and 2.57M t-butyl hydroperoxide solution in isooctane (0.58 ml, 1.5 mmol) was added. The reaction was stirred at −20° C. for 6 hours, at which time the molecular sieves were removed by filtration. The filtrate was quenched by pouring into a stirred 50 ml solution prepared from citric acid monohydrate (3.3 g), ferrous sulfate heptahydrate (9.9 g), and deionized water. Stirring was continued for 30 minutes, then the layers were left to separate. The aqueous layer was extracted with an equal volume of methylene chloride. The original methylene chloride layer and the methylene chloride extract were combined and dried over sodium sulfate. Evaporation of the solvent followed by NMR analysis of a deuterated chloroform (CDCl) solution of the residue showed a 31/69 ratio of starting material to sulfoxide products (67/33 mixture of sulfoxide diastereomers). The evaporation residue was chromatographed on silica gel. Elution with 6 L of a 10–50% ethyl acetate in hexane gradient yielded optically enriched starting material (0.26 g, 29% recovery) as a white foam: ee 34% (HPLC);

Elemental Analysis for $C_{20}H_{31}NO_2S$: Theory: C, 68.72; H, 8.94; N, 4.01. Found: C, 68.95; H, 8.92; N, 4.23.

EXAMPLE 3

Preparation of (Z)-2-[[3,5-bis(1,1-dimethylethyl)-4-hydroxyphenyl]methylene]-4-methyl-3-thiomorpholinone.

A. Preparation of pivaloyl protected 3,5-di-t-butyl-4-hydroxy benzaldehyde

To a stirred solution of 3,5-di-t-butyl-4-hydroxy benzaldehyde (213.2 g, 910 mmole) in dichloromethane (2.73 L) was added triethylamine (139.5 ml, 1 mole). Then a solution of pivaloyl chloride (123.3 ml, 1 mole) in dichloromethane (455 ml) was added while the reaction temperature was maintained at 25° C. with an ice bath. After an additional 10 min of stirring the reaction was extracted with 1.8 L of water. The organic layer was dried over sodium sulfate, evaporated to dryness, and used without further purification.

B. Preparation of the lithium enolate of 4-methyl-3-thiomorpholinone n-Butyl lithium in hexane (135.5 ml, 182 mmole) was added to 4-methyl-3-thiomorpholinone (23.88 g, 182 mmole) (prepared as in Example 1A) in tetrahydrofuran (546 ml) at 0° C. over 6 minutes. The reaction was allowed to stir for 3 minutes before the ice bath was removed. After an additional 10 minutes the solution was cooled to −78° C. and kept at that temperature until ready for use.

C. Preparation of (Z)-2-[[3,5-bis(1,1-dimethylethyl)-4-hydroxyphenyl]methylene]-4-methyl-3-thiomorpholinone.

To a tetrahydrofuran (1.27 L) solution of the protected benzaldehyde, prepared above in Step A, which was cooled to −78° C., was added the enolate solution, prepared above in Step B, over 30 minutes. The reaction was allowed to stir an additional 1 hour at −78° C., then poured into 910 ml water and extracted with ethyl acetate. The organic layer was extracted with brine, dried over sodium sulfate, and evaporated to dryness. The residue was triturated with dichloromethane and filtered to remove recovered 3,5-di-t-butyl-4-hydroxy benzaldehyde. The filtrate was chromatographed on silica gel using a 5–30% acetone in hexane gradient to yield desired product (30.4 g, 48%):

$^1$H NMR (CDCl$_3$) ∂ 7.9 (s, 1H), 7.5 (s, 2H), 5.45 (s, 1H), 3.8 (m, 2H), 3.2 (s, 3H), 2.0 (m, 2H), 1.5 (s, 18H);

FD MS 347 (M$^+$);

Elemental Analysis for $C_{20}H_{29}NO_2S$: Theory: C, 69.12; H, 8.41; N, 4.04. Found: C, 69.41; H, 8.33; N, 3.76.

EXAMPLE 4

Preparation of (Z)-2-[[3,5-bis(1,1-dimethylethyl)-4-hydroxyphenyl]methylene]-4-methyl-3-thiomorpholinone-1-oxide.

A solution of (Z)-2-[[3,5-bis(1,1-dimethylethyl)-4-hydroxyphenyl]methylene]-4-methyl-3-thiomorpholinone (1.25 g, 3.6 mmol) in dichloromethane (18 ml) was cooled under nitrogen to 0° C. A solution of m-chloroperoxybenzoic acid (0.78 g, 3.6 mmol) in dichloromethane (11ml) was then added dropwise over 5 minutes. The reaction mixture was stirred an additional 25 minutes and washed once with saturated sodium bicarbonate. The organic layer was dried over sodium sulfate. Rotary evaporation gave crude product which was crystallized from ethyl acetate-hexane to give desired product (1.04 g, 79%):

$^1$HNMR (CDCl$_3$) ∂ 8.45 (s, 1H), 7.65 (s, 2H), 5.7 (S, 1H), 4.65 (ddd, J=12, 12, 2 Hz, 1H), 3.5 (ddd, J=12, 2, 2 Hz, 1H), 3.2 (s, 3H), 3.15 (m, 1H), 2.95 (ddd J=12, 12, 2 Hz, 1H), 1.5 (s, 18H);

FD MS 363 (M$^+$);

Elemental Analysis for $C_{20}H_{29}NO_3S$: Theory: C, 66.08; H, 8.04; N, 3.85. Found: C, 66.18; H, 8.09; N, 3.88.

EXAMPLE 5

Preparation of (Z)-2-[[3,5-bis(1,1-dimethylethyl)-4-hydroxyphenyl]methylene]-4-methyl-3-thiomorpholinone-1,1-dioxide.

A solution of (Z)-2-[[3,5-bis(1,1-dimethylethyl)-4-hydroxyphenyl]methylene]-4-methyl-3-thiomorpholinone (1.25 g, 3.6 mmol) in dichloromethane (18 ml) was cooled under nitrogen to 0° C. A solution of m-chloroperoxybenzoic acid (1.55 g, 7.2 mmol) in dichloromethane (22 ml) was then added dropwise over 15 minutes. The reaction was allowed to stir at room temperature for 20 hours and washed twice with saturated sodium bicarbonate. The organic layer was washed once with brine and dried over sodium sulfate. Rotary evaporation gave crude product which was crystallized from ethyl acetate-hexane, then recrystallized from dichloromethane-hexane to give desired product (1.15 g, 84%) as the dichloromethane solvate:

$^1$H NMR (CDCl$_3$) ∂ 8.4 (S, 1H), 7.85 (S, 2H), 5.8 (S, 1H), 5.3 (s, 2H), 3.85 (m, 2H), 3.4 (m, 2H), 3.2 (s, 3H), 1.5 (s, 18H);

FD MS 379 (M$^+$);

Elemental Analysis for $C_{20}H_{29}NO_4S \cdot CH_2Cl_2$: Theory: C, 54.55; H, 6.83; N, 3.01. Found: C, 54.30; H, 6.74; N, 3.02.

EXAMPLE 6

Preparation of (Z)-2-[[3,5-bis(1,1-dimethylethyl)-4-hydroxyphenyl]methylene]-4-ethyl-3-thiomorpholinone.

Title compound was prepared substantially according to the procedure for Example 3 given above:

$^1$H NMR (CDCl$_3$) ∂ 7.84 (S, 1H), 7.47 (S, 2H), 5.41 (s, 1H), 3.77 (m, 2H), 3.59 (q, J=8 Hz, 2H), 2.99 (m, 2H), 1.46 (s, 18H), 1.23 (t, J=8 Hz, 3H);

FD MS 361 (M$^+$);

Elemental Analysis for $C_{21}H_{31}NO_2S$: Theory: C, 69.77; H, 8.64; N, 3.87. Found: C, 70.05, H, 8.60; N, 3.61.

Experimental Autoimmune Encephalomyelitis (EAE) Model

Experimental autoimmune encephalomyelitis (EAE) is an inflammatory autoimmune demyelinating disease which can be induced in laboratory animals by injection of myelin basic protein. Such disease has become the standard laboratory model for studying clinical and experimental autoimmune diseases. In fact, numerous articles [e.g., Abramsky, et al., *J. Neuroimmunol.*, 2, 1 (1982) and Bolton et al., *J. Neurol. Sci.*, 56, 147 (1982)] note that the similarities of chronic relapsing EAE in animals to multiple sclerosis in humans especially implicates the value of EAE for the study of autoimmune demyelinating diseases such as multiple sclerosis. As such, the EAE test model was employed to establish the activity of the compounds of formula I against multiple sclerosis. Such testing was conducted according to the following procedure.

Female Lewis rats (Olac Ltd., U.K.), were injected in their footpads with 12.5 mg of myelin basic protein (MBP) (prepared from guinea-pig spinal cord) in Complete Freunds adjuvant. Test compound was given daily from day 0 (MBP injection date) in carboxymethylcellulose p.o. at a dosage of 33 mg/kg to the test animals. A control solution (carboxymethylcellulose alone) was given to certain other test animals. The animals were then weighed and scored daily for symptoms of EAE according to a scale of 0 to 3 (0=no change; 1=flaccid tail; 2=hind limb disability and 3=hind quarter paralysis/moribund). Animals were sacrificed when they reached a score of 3.

The results of the experiment described above are set forth in Table I, below. In Table I, Column 1 indicates the example number of the test compound employed or, if appropriate, that no test compound was employed (control). Columns 2–16 report the EAE disease score associated with various times after the MBP injection date (day 0).

TABLE I

Inhibition of EAE

| Compound Example No./ Control | EAE Disease Score At Various Days After MBP Administration* | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Control | 0 | 0 | 0 | 0 | 0 | 0 | 0 | 0 | 0.13 | 0.25 | 1.38 | 2.75 | 3 | 3 | 3 |
| Example 3 | 0 | 0 | 0 | 0 | 0 | 0 | 0 | 0 | 0 | 0.5 | 0.5 | 2.2 | 2.4 | 2.4 | 2.4 |

*EAE Disease Score based on an average of 6 test animals.

The results set forth in Table I, above, establish that, given the proper dosing paradigm, the compounds of formula I inhibit the progression of EAE. As such, the compounds of formula I would be expected to be efficacious in treating multiple sclerosis.

Pharmaceutical Formulations

As noted above, the compounds of formula I are capable of s low ing the process of neurodegeneration associated with multiple sclerosis, thereby lending themselves to the valuable therapeutic method claimed herein. This method comprises administering to a mammal in need of treatment for multiple sclerosis an amount of one or more compounds of formula I sufficient to achieve the therapeutic effect desired. The compounds can be administered by a variety of routes including the oral, rectal, transdermal, subcutaneous, intravenous, intramuscular or intranasal routes. The oral and transdermal routes of administration are preferred. No matter what route of administration is chosen, such administration is accomplished by means of pharmaceutical compositions which are prepared by techniques well known in the pharmaceutical sciences.

In making the pharmaceutical compositions, one or more active ingredients will usually be mixed with a carrier, or diluted by a carrier, or enclosed within a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions may be formulated so as to provide rapid, sustained or delayed release of the active ingredient after administration to the patient by employing procedures well known in the art.

The compositions are formulated, preferably in a unit dosage form, such that each dosage contains from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with one or more suitable pharmaceutical diluents, excipients or carriers.

The compounds utilized in the method of the present invention are effective over a wide dosage range for the treatment of multiple sclerosis. Thus, as used herein, the term "therapeutically effective amount" refers to a dosage range of from about 0.5 to about 50 mg/kg of body weight per day. in the treatment of adult humans, the range of about 1 to about 10 mg/kg, in single or divided doses, is preferred. However, it will be understood that the amount of the compound actually administered will be determined by a physician, in the light of the relevant circumstances including the choice of compound to be administered, the chosen route of administration, the age, weight, and response of the individual patient, and the severity of the patient's symptoms, and therefore the above dosage ranges are not intended to limit the scope of the invention in any way.

Multiple sclerosis can exist as either an acute or chronic condition. The term "acute" means an exacerbated condition of short course followed by a period of remission. The term "chronic" means a deteriorating condition of slow progress and long continuance. Symptoms are myriad, depending upon the area in the brain where lesions occur, and can occur anywhere in the body. Symptoms may include such conditions as weakness, blindness, speech difficulties, sensory changes, memory change and so forth. It is contemplated that the present invention encompasses the treatment of both acute and chronic forms of multiple sclerosis. In the acute form, compound is administered at the onset of symptoms and discontinued when the symptoms disappear. A chronic condition is treated when it is diagnosed as chronic and continued throughout the course of the disease.

The following formulation examples may employ as active ingredients any of the compounds of formula I. The examples are illustrative only and are not intended to limit the scope of the invention in any way.

Formulation 1

Hard gelatin capsules are prepared using the following ingredients:

| | Quantity (mg/capsule) |
|---|---|
| 2-[[3,5-bis(1,1-dimethylethyl)-4-hydroxyphenyl]methylene]-4-(2-hydroxyethyl)-3-thiomorpholinone | 500 |
| Starch dried | 200 |
| Magnesium | 10 |

The above ingredients are mixed and filled into hard gelatin capsules in 710 mg quantities.

Formulation 2

A tablet formula is prepared using the ingredients below:

| | Quantity (mg/capsule) |
|---|---|
| 2-[[3,5-bis(1,1-dimethylethyl)-4-hydroxyphenyl]methylene]-4-[2-(dimethylamino)ethyl]-3-thiomorpholinone | 100 |
| Cellulose, microcrystalline | 400 |
| Silicon dioxide, fumed | 10 |
| Stearic acid | 5 |

The components are blended and compressed to form tablets each weighing 515 mg.

Formulation 3

Tablets each containing 50 mg of active ingredient are made up as follows:

| | Quantity (mg/capsule) |
|---|---|
| 2-[[3,5-bis(1,1-dimethylethyl)-3-hydroxyphenyl]methylene]-4-(methylsulfonyl)-3-thiomorpholinone | 50 mg |
| Starch | 50 mg |
| Microcrystalline cellulose | 40 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50–60° C. and passed through a No. 18 mesh U.S. sieve. The sodium carboxymethyl starch, magnesium stearate and talc, previously passed through a No. 60 mesh U.S. Sieve, are then added to the granules which, after mixing, are compressed by a tablet machine to yield tablets each weighing 150 mg.

Formulation 4

Capsules each containing 25 mg of medicament are made as follows:

| | Quantity (mg/capsule) |
|---|---|
| 2-[(4-hydroxy-3,5-di-2-propenylphenyl)methylene]-4-methyl-3-thiomorpholinone | 25 mg |
| Starch | 60 mg |
| Microcrystalline cellulose | 60 mg |
| Magnesium stearate | 5 mg |
| Total | 150 mg |

The active ingredient, cellulose, starch and magnesium stearate are blended, passed through a No. 45 mesh U.S. sieve, and filled into hard gelatin capsules in 200 mg quantities.

Formulation 5

Suppositories each containing 250 mg of active ingredient are made up as follows:

| | Quantity (mg/capsule) |
|---|---|
| 2-[(4-hydroxy-3,5-dinitrophenyl)methylene]-4-methyl-3-thiomorpholinone; | 250 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 6

Suspensions each containing 100 mg of medicament per 5 ml dose are made as follows:

| | Quantity (mg/capsule) |
|---|---|
| 2-[(3,5-dichloro-4-hydroxyphenyl)methylene]-4-methyl-3-thiomorpholinone; | 100 mg |
| Sodium carboxymethylcellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 7

Capsules each containing 5 mg of medicament are made up as follows:

| | Quantity (mg/capsule) |
|---|---|
| 2-[(3,5-dichloro-4-hydroxyphenyl)methylene]-4-methyl-3-thiomorpholinone; | 5 mg |
| Starch | 164 mg |
| Microcrystalline cellulose | 164 mg |
| Magnesium stearate | 22 mg |
| Total | 355 mg |

The active ingredient, cellulose, starch and magnesium stearate are blended, passed through a No. 45 mesh U.S. sieve, and filled into hard gelatin capsules in 355 mg quantities.

We claim:

1. A method for treating multiple sclerosis in a mammal in need of such treatment which comprises administering to said mammal a therapeutically effective amount of a compound of formula I

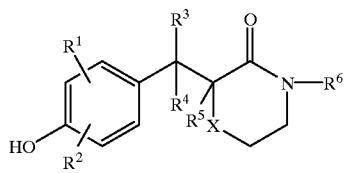

(I)

wherein:

$R^1$ and $R^2$ are each independently selected from $C_1$–$C_8$ alkyl; $C_2$–$C_8$ alkenyl; $C_2$–$C_8$ alkynyl; $C_1$–$C_8$ alkyloxy; $C_1$–$C_8$ alkylthio; trifluoromethyl; $C_1$–$C_4$ alkyl substituted with phenyl; phenyl; F; Cl; $NO_2$; phenoxy; $C_1$–$C_4$ alkyl substituted with phenoxy; thiophenyl; $C_1$–$C_4$ alkylthiophenyl; —$COOR^7$; —$N(R^7)_2$ or —$N(R^7)SO_2R^7$ where each $R^7$ is independently hydrogen or $C_1$–$C_6$ alkyl;

$R^3$ is H or $C_1$–$C_4$ alkyl;

$R^4$ and $R^5$ are each individually H, or when taken together form a bond;

$R^6$ is H; $C_1$–$C_8$ alkyl; $C_2$–$C_8$ alkenyl; $C_2$–$C_8$ alkynyl; —$SO_2CH_3$; —$(CH_2)_nNR^8R^9$; —$(CH_2)_nCO_2R^8$; —$(CH_2)_nOR^8$ where n is an integer from 1 to 6, both inclusive, and $R^8$ and $R^9$ are each independently hydrogen; $C_1$–$C_6$ alkyl; $C_2$–$C_6$ alkenyl; $C_2$–$C_6$ alkynyl; phenyl; $C_1$–$C_4$ alkyl substituted with phenyl; —$(CH_2)_q$OH; or $(CH_2)_qS(C_1$–$C_4$alkyl) where q is an integer from 2 to 6, both inclusive; and X is 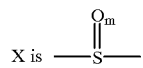

where m is 0 or 1;

or a pharmaceutically acceptable salt or optical isomer thereof.

2. The method of claim 1 wherein $R^6$ is hydrogen, $C_1$–$C_6$ alkyl $C_2$–$C_6$ alkenyl or —$(CH_2)_nOR^8$ where n is 2 and $R^8$ is hydrogen;

X is 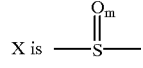

where m is 0; and $R^1$ and $R^2$ are each independently selected from $C_1$–$C_8$ alkyl or $C_1$–$C_8$ alkoxy.

3. The method of claim 1 wherein the compound is 2-[[3,5-bis(1,1-dimethylethyl)-4-hydroxyphenyl]methyl]-4-methyl-3-thiomorpholinone.

4. A method of claim 1 wherein the compound is (−)2-[[3,5-bis(1,1-dimethyl ethyl)-4-hydroxy phenyl]methyl]-4-methyl-3-thiomorpholinone.

* * * * *